US011844824B2

(12) United States Patent
Narayanan et al.

(10) Patent No.: US 11,844,824 B2
(45) Date of Patent: Dec. 19, 2023

(54) NUCLEIC ACID MOLECULES AND METHODS OF USING THE SAME

(71) Applicant: PEPVAX, INC., Bethesda, MD (US)

(72) Inventors: Mahesh Narayanan, Thorofare, NJ (US); Anton Dormer, Bowie, MD (US)

(73) Assignee: PEPVAX, INC., Bethesda, MD (US)

( * ) Notice: Subject to any disclaimer, the term of this patent is extended or adjusted under 35 U.S.C. 154(b) by 0 days.

(21) Appl. No.: 16/978,106

(22) PCT Filed: Mar. 6, 2019

(86) PCT No.: PCT/US2019/020929
§ 371 (c)(1),
(2) Date: Sep. 3, 2020

(87) PCT Pub. No.: WO2019/173462
PCT Pub. Date: Sep. 12, 2019

(65) Prior Publication Data
US 2021/0015894 A1    Jan. 21, 2021

Related U.S. Application Data

(60) Provisional application No. 62/639,092, filed on Mar. 6, 2018.

(51) Int. Cl.
*A61K 38/16*     (2006.01)
*C12N 15/113*    (2010.01)
*C12N 15/63*     (2006.01)

(52) U.S. Cl.
CPC ............ *A61K 38/16* (2013.01); *C12N 15/113* (2013.01); *C12N 15/63* (2013.01); *C12N 2310/11* (2013.01)

(58) Field of Classification Search
CPC ..... C12N 15/62; C12N 15/63; C07K 2319/02
USPC ................. 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 5,683,904 A * | 11/1997 | Baker ............. | C12P 21/06 435/219 |
| 2003/0096778 A1 | 5/2003 | Shiver et al. | |
| 2003/0109475 A1 | 6/2003 | Debs et al. | |
| 2004/0265325 A1 | 12/2004 | Diamond et al. | |
| 2005/0215508 A1 | 9/2005 | Shiver et al. | |
| 2006/0121051 A1 | 6/2006 | Kenten et al. | |
| 2006/0154885 A1 | 7/2006 | Bennett et al. | |
| 2006/0194754 A1 | 8/2006 | deJong et al. | |
| 2009/0041804 A1* | 2/2009 | Schlom ............ | C07K 14/70525 424/229.1 |
| 2009/0221682 A1 | 9/2009 | Maithal et al. | |
| 2010/0074925 A1* | 3/2010 | Carmon ............ | C07K 14/4748 424/277.1 |
| 2011/0135596 A1* | 6/2011 | Lee ................. | C12N 15/62 435/69.51 |
| 2012/0238496 A1 | 9/2012 | Fan et al. | |
| 2013/0216495 A1 | 8/2013 | Motlagh et al. | |
| 2016/0031946 A1 | 2/2016 | Derouazi et al. | |
| 2018/0028626 A1* | 2/2018 | Slos ................. | C07K 16/3046 |

FOREIGN PATENT DOCUMENTS

| | | |
|---|---|---|
| WO | 9117245 | 11/1991 |
| WO | 2010084100 A1 | 7/2011 |

OTHER PUBLICATIONS

International Search Report and Written Opinion, dated May 14, 2019, issued in corresponding International Application No. PCT/US2019/020929, filed Mar. 6, 2019.
Kirilyuk et al., "Functional endogenous LINE-1 retrotransposons are expressed and mobilized in rat chloroleukemia cells", Nucleic Acids Res., 36: 648-665 (2007).
Clontech: "pAcGFP1-Nuc Vector Information," Clontech Laboratories, Inc. (Mar. 27, 2003) Protocol No. PT3729-5, Version No. PR33644, pp. 1-3.
De Jong et al., "A Novel Platform for the Potentiation of Therapeutic Antibodies Based on Antigen-Dependent Formation of IgG Hexamers at the Cell Surface," PLOS Biology (Jan. 6, 2016), pp. 1-24.
European Search Report for European Patent Application No. 19763485.0 dated Jan. 4, 2022.
Xiao et al., "Engineering Nanoparticles for Targeted Delivery of Nucleic Acid Therapeutics in Tumor," Molecular Therapy: Methods & Clinical Development (Mar. 2019) vol. 12, pp. 1-18.
Japanese Office Action issued for Japanese Patent Application No. 2020-570409 with English Translation (dated Jan. 31, 2023).

\* cited by examiner

*Primary Examiner* — Jane J Zara
(74) *Attorney, Agent, or Firm* — Troutman Pepper Hamilton Sanders LLP (Rochester)

(57) ABSTRACT

Nucleic acid molecules are provided herein that can be used, for example, to treat cancer or infections, or to induce an immune response in a subject, or to deliver or express a target molecule in or from a cell.

5 Claims, 2 Drawing Sheets

Specification includes a Sequence Listing.

Control vector (pCDNA2.1-CMV-GFP)

(pV3X-Venus GFP_element 1 vector)

NUCLEIC ACID MOLECULES AND METHODS OF USING THE SAME

BACKGROUND

Immunotherapy and gene therapy has revolutionized the treatments of various diseases. However, the therapies are still imperfect and thus, there is a need to provide new therapies that overcome the disadvantages and shortcoming still present today. The present disclosure fulfills these needs as well as others.

SUMMARY

In some embodiments, nucleic acid molecules are provided. In some embodiments, the nucleic acid molecule comprises a polynucleotide comprising a sequence encoding a constitutive promoter, a sequence encoding an amino acid sequence of a target full-length protein or a sequence encoding a target molecule. In some embodiments, the molecule comprises a sequence encoding an amino acid sequence of a linker. In some embodiments, the molecule comprises a sequence encoding an amino acid sequence of ubiquitin. In some embodiments, the molecule comprises a sequence encoding a fragment, such as a fragment of at least 7 amino acid residues of the target protein or target protein. In some embodiments, the molecule comprises a sequence encoding a nuclear localization signal. In some embodiments, the nucleotide sequences are operatively connected one another. In some embodiments, the molecule comprises a sequence that encodes a polypeptide comprising a full length protein, a linker, a ubiquitin protein, and a fragment of the full length protein. In some embodiments, instead of a full length protein and a fragment of the same, the nucleic acid molecule encodes two fragments of the same protein, with the fragments being different lengths or sequences, although there can be overlap in the fragments. In some embodiments, the fragment is not encoded for. In some embodiments, when the fragment is not encoded for, the sequences encoding for the linker and the ubiquitin are optional and the molecule can be free of such sequences.

In some embodiments, the various components that are expressed are operatively connected to one another to encode a protein or target molecule. For example, in some embodiments, the sequence that encode for a protein comprising the amino acid sequence of the full-length protein; the amino acid sequence of the linker, the amino acid sequence of ubiquitin, and at least 7 amino acid residues of the target protein are operatively connected to one other so that each is expressed.

In some embodiments, pharmaceutical composition comprising the nucleic acid molecules provided herein are provided. In some embodiments, the pharmaceutical compositions comprises a pharmaceutically acceptable excipient or carrier. In some embodiments, the composition comprises additional therapeutics, such as antibodies that bind to PD-1, PD-L1, TNF-alpha, CTL4, and the like. Other types of therapeutics can also be combined with the nucleic acid molecules provided for herein.

In some embodiments, methods of inducing an immune response against a protein in a subject are provided. In some embodiments, the methods comprise introducing (e.g., administering) a nucleic acid molecule provided herein into a cell of the subject. In some embodiments, the nucleic acid molecule is expressed in the cell and an immune response is induced against the target protein encoded by the nucleic acid mole.

In some embodiments, methods of treating cancer in a subject are provided. In some embodiments, the method comprises introducing (e.g. administering) the nucleic acid molecules provided herein into the subject to treat the cancer. In some embodiments, the target protein encoded by the nucleic acid molecule is a protein that is overexpressed in a cancer cell or tumor.

In some embodiments, methods of inhibiting an infectious agent or an infection in a subject are provided. In some embodiments, the methods comprise introducing (e.g. administering) the nucleic acid molecules provided herein into the subject to inhibit the infection agent or to treat the infection in the subject. In some embodiments, the target protein encoded by the nucleic acid molecule is a protein that is expressed by the infectious agent.

In some embodiments, methods of expressing or delivering a target molecule are provided. In some embodiments, the methods comprise introducing (e.g. administering) or contacting a cell or a subject with the nucleic acid molecules provided herein to express or deliver the target molecule to the cell. In some embodiments, the target molecule is secreted from the cell.

In some embodiments, a cell comprising the nucleic acid molecules provided for herein are provided. In some embodiments, the cell is an isolated cell. In some embodiments, the cell is ex-vivo and not in a subject.

DETAILED DESCRIPTION

Figure 1:
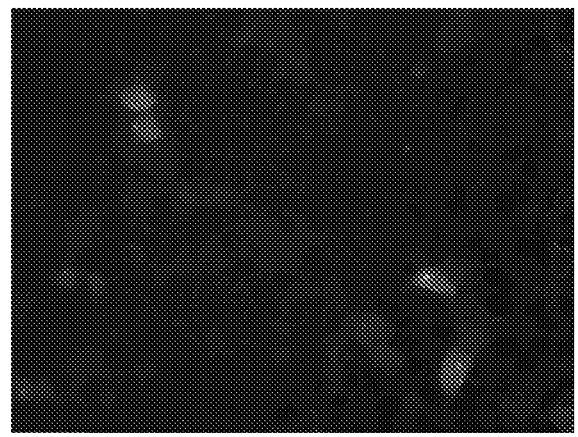
FIG. 1 illustrates the data of an experiment performed, wherein equimolar amounts of plasmid DNA was transfected onto identical cultures of HEK-293 human embryonic kidney cells and GFP expression was monitored 24 hours post-transfection. The top panel illustrates the control and the lower panel illustrates the expression of GFP from the cells.
Figure 1:
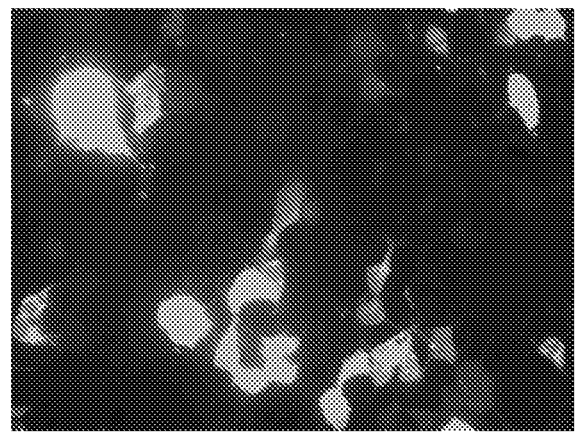

Embodiments provided for herein provide a platform that can, for example, allow for the integration of foreign nucleotides that can be expressed as immunogens or target molecules. The expression of immunogens or molecules can be used, for example, in methods to prevent or treat cancer and/or infectious diseases. In some embodiments, nucleic acid molecules provided herein can be used to assemble a number of DNA fragments into one nucleic acid molecule. This can be done, for example, in spite of restriction sites redundancy found at the ends and within the DNA fragments. The nucleic acid molecules provided herein can also comprise a nucleus uptake component, such as a nuclear localization signal (domain) that can facilitate the rapid plasmid integration or uptake within the nucleus. This update can lead to an immunological response.

For example, the nucleic acid molecules provided for herein can cross the cell membrane and transfects the nucleus. Once that process occurs the foreign nucleotide is then expressed by the host's cell transcription and translation process. A "foreign nucleotide" is one that is introduced into the cell and is not native to the cell's genome. Examples include any of the nucleic acid molecules provided for herein and examples also include plasmids or other types of vectors provided herein. After translation, the antigen when it has reached the cell surface can be presented in conjunction with a major histocompatibility complex protein class I or class II. Without being bound by any particular theory, the antigen presenting cell (APC), such as a macrophage or dendritic cell, would take that foreign antigen and travel to a lymph node where the APC will present the antigenic target protein and/or fragment which then lead to an immune response to the antigen encoded for by the nucleic acid molecules provided herein.

It must also be noted that as used herein, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%. The present disclosure modifies certain terms or values with the term "about," however, the disclosure should also be understood to disclose the exact value as well and is simply not written out for convenience. For example, the phrase "about 9 to about 25" also discloses "9 to 25." Additionally, a range, such the phrase "from X to Y" where X and Y are any integer includes the endpoints. For example, the phrase "from 1 to 5" means 1, 2, 3, 4, or 5.

"Administering" when used in conjunction with a therapeutic means to administer a therapeutic directly into or onto a target tissue or to administer a therapeutic to a patient. Non-limiting examples of methods of administration that can be used to administer nucleic acid molecules, include, but are not limited to, transfection, electroporation, injection, sonication, or by any method in combination with other known techniques. Such combination techniques include heating and radiation. In some embodiments, the nucleic acid molecule is delivered to a muscle cell. This can be done, for example, by electroporation or other suitable technique. Electroporation of the nucleic acid molecule to the muscle or other tissue type can be done, for example, using a electroporation device.

The term "animal" as used herein includes, but is not limited to, humans and non-human vertebrates such as wild, domestic and farm animals.

The term "cloning" is used in reference to the ligating process of a nucleic acid molecule into a another nucleic acid molecule, such as a plasmid. The cloned molecule can then be transferred into a host cell or subject for duplication, amplification, or administration.

The terms "cloning vector" and "cloning vector plasmid" are used to refer to a circular DNA plasmid which contains in minimum an origin of replication. The origin of replication can be used to positively select host cells that harbor the plasmid and could be an antibiotic resistance gene or a multiple cloning site.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "genetic construct" refers to the DNA or RNA molecule that comprises a nucleotide sequence which encodes the target protein or target molecule and which includes initiation and termination signals operably linked to regulatory elements including a promoter and polyadenylation signal capable of directing expression in the cells of the vaccinated individual. In some embodiments, the nucleic acid molecules provided herein are in the form of a plasmid or viral vector. In some embodiments, the genetic construct is a plasmid or a viral vector. In some embodiments, the genetic construct does not contain integration elements. In some embodiments, the plasmid does not contain, or is free of, any inverted terminal repeats or other sequences that would facilitate the integration of the plasmid into the subject's, or cell's, genome. In some embodiments, the plasmid is a non-integrating plasmid. A non-integrating plasmid, is a plasmid that is not designed to integrate into a genome of the subject or a cell that comes into contact the plasmid. In some embodiments, the non-integrating plasmid is contacted with a cell without any other components that would facilitate the integration of the plasmid into a genome. For example, plasmids can be used in conjunction with gene editing platforms, such as CRISPR, that can be used to integrate portions of the plasmid into the genome. Therefore, in some embodiments, the plasmid can be used without CRISPR or CRISPR like enzyme, such as CAS9 and the like.

As used herein, "DNA construct" refers to a DNA molecule that is synthesized by the cloning steps that are consecutive with a cloning vector plasmid. This is the process that is commonly used as a means to direct gene expression to an appropriate mammalian host. This mammalian host could be cells that have been cultured in vitro or transgenic mice in vivo.

The term "DNA fragment" refers to any DNA molecule isolation that include but is not limited to the different parts of the plasmid such as the intron, exon, reporter gene, poly A tail, and the different cloning sites. These DNA fragment could also include signal nucleotides, such as, the mRNA stabilization signal and the nuclear localization signal. Plasmid vector can comprise of naturally and synthetic DNA fragments.

The term "enhancer region" refers to the sequence of nucleotides that are not required for targeted gene expression, but is designed to increase the gene expression levels.

As used herein, the term "expressible form" refers to gene constructs which contain the necessary regulatory elements operably linked to a coding sequence that encodes a target protein or target molecule, such that when present in the cell of the individual, the coding sequence will be expressed.

The terms "gene promoter" or "promoter" as used herein refer to and is in reference to a sequence of nucleotides that is required for gene expression.

As used herein, the term "genetic vaccine" refers to a pharmaceutical preparation that comprises a genetic construct that comprises a nucleotide sequence that encodes a target protein or target molecule and can include pharmaceutical preparations useful to invoke a therapeutic immune response. In some embodiments, the nucleotide sequence encodes a shRNA, siRNA, antisense, antibodies, hormones, insulin, and the like. Other target molecules can also be encoded for as described herein, such as, but not limited to, adjuvants.

As used herein, the term "genetic therapeutic" refers to a pharmaceutical preparation that comprises a genetic construct that comprises a nucleotide sequence that encodes a therapeutic or compensating protein.

The term "inhibiting" includes the administration of a plasmid or nucleic acid molecule prevent the onset of the symptoms, alleviate the symptoms, reduce the symptoms, delay or decrease the progression of the disease and/or its symptoms, or eliminating the disease, condition or disorder.

The term "nuclear localization signal" is used to refer to sequences of nucleotides that encode a signal of subcellular routing of proteins of interest to a nucleus of a cell. The nuclear localization signal can also be used to direct transport of a nucleic acid molecule to the nucleus of the cell.

As used herein, the terms "origin of replication" or "ORI" refer to sequences of nucleotides that can direct or lead to host cell duplication of a plasmid.

By "pharmaceutically acceptable," it is meant the carrier, diluent or excipient must be compatible with the other ingredients of the formulation and not deleterious to the recipient thereof.

As used herein, the term "poly A tail" is in reference to the nucleotide sequence of adenine (A) nucleotides. These nucleotides are usually found at the terminal end of the messenger RNA molecule (mRNA). The poly-A tail is incorporated at the 3' of the end of the DNA construct that allows for enhancement of the gene expression of interest. In some embodiments, the nucleic acid molecules provided herein comprise a poly A tail.

As used herein, the term "reporter gene" is in reference to the sequence of nucleotides that encode a protein useful in the activity of monitoring the promoter of particular interest. Examples of reporter genes include fluorescent proteins, such as GFP and SEAP.

As used herein, the terms "tag sequence" or "Tag" refer to sequences of nucleotides that encode a protein or peptide region that is unique, which allow for it to be detected and distinguished from any endogenous counterpart. Non-limiting examples of tags include His tag, GST tag, Calmodulin Binding Protein (CBP), Maltose-binding protein (MBP), myc tag, HA tag, FLAG tag, and the like.

As used herein, the term "target protein" can refer to a protein against which an immune response can be elicited and is desired to be elicited against. The target protein can be, for example, an immunogenic protein or fragment thereof, which shares at least an epitope with a protein from the pathogen or undesirable cell-type such as a cancer cell. The immune response directed against the target protein can be used to induce the immune response that will protect the individual against and treat the individual for the specific infection or disease with which the target protein is associated. In some embodiments, the target protein that is a cell surface protein or an protein (antigen) that is secreted from the cell. In some embodiments, these types of proteins or antigens can be used to elicit an activated immune response from a T-cytotoxic lymphocytes or CD8+ immune cells. For example, these types of proteins or antigens can processed by the major histocompatibility complex (MHC) class I pathway, which interacts with CD8+ immune cells. The presentation of proteins/antigens through this pathway can be facilitated, for example, by the addition of ubiquitin moieties at the N terminal end of the target protein. As described herein, the nucleic acid molecule can encode a target protein that is linked to, fused to (in frame), or conjugated with a ubiquitin moiety.

A "target protein" can also refer to a protein that is expressed in, or secreted from, a cell. The target protein can be a receptor, an antibody, a chimeric antigen receptor (CAR), a hormone, such as insulin, and the like.

The nucleic acid molecules described herein can also be used to express different types of target molecules, such as nucleic acid molecules provided for herein, which includes, but are not limited to shRNA, siRNA, antisense, microRNAs, and the like.

As used herein, the term "therapeutic" means an agent utilized to treat, combat, ameliorate, prevent or improve an unwanted condition or disease of a patient. In part, embodiments are directed to the treatment of cancer or the decrease in proliferation of cells. In part, embodiments are directed to the treatment of infections or infectious agents.

A "therapeutically effective amount" or "effective amount" of a therapeutic is a predetermined amount calculated to achieve the desired effect, i.e., stimulate an immune response. The activity contemplated by the present methods includes both medical therapeutic and/or prophylactic treatment, as appropriate.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results.

The term "untranslated region" refers to the sequences of nucleotides that cover the nucleotide region that does not code for a protein found within a mRNA molecule. These regions that are not translated can be found at the 5' and 3' regions of the mRNA molecule. In some embodiments, the nucleic acid molecule provided herein that encodes a target protein or a fragment of the target protein comprises an untranslated region.

In some embodiments, the nucleic acid molecule and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose with a specific intent.

In some embodiments, the nucleic acid sequence comprises: a sequence encoding a constitutive promoter, a sequence encoding an amino acid sequence of a target full-length protein, a sequence encoding an amino acid sequence of a linker, a sequence encoding an amino acid sequence of ubiquitin, a sequence encoding at least 7 amino acid residues of the target protein, and a sequence encoding a nuclear localization signal, wherein the sequences are operatively connected to one another and the sequences of b), c), d), and e) are operatively connected to one another to encode a protein comprising the amino acid sequence of the full-length protein; the amino acid sequence of the linker, the amino acid sequence of ubiquitin, and at least 7 amino acid residues of the target protein. In some embodiments, the fragment is about 7 to about 25 amino acids in length. In some embodiments, the fragment is at about 7 to about 15, about 7 to about 12, about 7 to about 10, about 7 to about 9 amino acids in length, or is 7, 8, 9, 10, 11, 12, 13, 14, 15, 16, 17, 18, 19, 20, 21, 22, 23, 24, or 25 amino acids in length.

In some embodiments, the nucleic acid molecules provided for herein do not contain or do not comprise (e.g. free of) a sequence encoding a fragment of a target protein, or alternatively, the nucleic acid molecule only encodes for one fragment of a target protein if the full length protein is not encoded for by the nucleic acid molecule.

In some embodiments, the nucleic acid sequence comprises a promoter. In some embodiments, the promoter is a constitutive promoter or a tissue specific promoter. A "tissue specific promoter" is a promoter that limits the expression or largely limits the expression to a specific tissue type. The promoter can also be a cell specific promoters so that the nucleic acid molecule's expression is limited to a specific cell or subset of cells. Examples of promoters that can be used include, but are not limited EF-1, SV40, Rous Sarcoma virus (RSV), Mason-Pfizer monkey virus-CTE, and CTE+ rev. In some embodiments, the EF-1 promoter is encoded by a sequence of:

```
                                               (SEQ ID NO: 1)
GACTCTTCGCGATTATCGCCGAATTCACGCGTCGTGAGGCTCCTGCAG

GGCCGACTAGTGGAGCCGAGAGTAATTCATACAAAAGGAGGGATCGC

CTTCGCAAGGGGAGAGCCCAGGGACCGTCCCTAAATTCTCACAGACCC

AAATCCCTGTAGCCGCCCCACGACAGCGCGAGGAGCATCCGCCCAGG

GCTGAGCGCGGGTAGATCAGAGCACACAAGCTCACAGTCCCCGGCGG

TGGGGGGAGGGGCGCGCTGAGCGGGGGCCAGGGAGCTGGCGCGGGG

CAAACTGGGAAAGTGGTGTCGTGTGCTGGCTCCGCCCTCTTCCCGAGG

GTGGGGGAGAACGGTATATAAGTGCGGTAGTCGCCTTGGACGTTCTTT

TTCGCAACGGGTTTGCCGTCAGAACGCAGCTGAAGCTTCGAGGGCTCG

CATCTCTCCTTCACGCGCCCGCCGCCCTACCTGAGGCCGCCATCCACG

CCGGTTGAGTCGCGTTCTGCCGCCTCCCGCCTGTGGTGCCTCCTGAACT

GCGTCCGCCGTCTAGGTAAGTTTAAAGCTCAGGTCGAGACCGGGCCTT

TGTCCGGCGCTCCCTTGGAGCCTACCTAGACTCAGCCGGCTCTCCACG

CTTTGCCTGACCCTGCTTGCTCAACTCTACGTCTTTGTTTCGTTTTCTGT

TCTGCGCCGTTACAGATCCAAGCCAGCTAGCGTTTAAACTTGCCGCCA

CC
```

These non-limiting examples of promoters can also be referred to as constitutive promoters. These non-limiting examples of promoters are known and can be incorporated into the nucleic acid molecule. However, this list is merely for example purposes only as there are numerous promoters that can be used to drive the expression of a target protein from the nucleic acid molecule. As provided for herein, the nucleic acid molecule encoding the promoter is operably connected to the nucleic acid molecule encoding the target protein to control, regulate, or drive the expression of the target protein in a cell.

In some embodiments, the nucleic acid molecule comprises a nucleic acid molecule encoding a target protein or target molecule. In some embodiments, the target protein is MAGE-A4, MAGE-A2, insulin, antibodies, hormones, chimeric antigen receptors, receptors, fusion proteins, GFP, SEAP, and the like. These target molecules can be expressed with or without the other elements of the plasmid, such as the ubiquitin, the fragment of the target molecule, the linker, and the like. In some embodiments, the antibody is a single chain antibody. In some embodiments, the antibody is a single domain antibody (sdAb). In some embodiments, the antibody is a scFV.

As provided for herein, the target molecule can be an antibody that is expressed from the nucleic acid molecule (e.g. plasmid). The term "antibody" as used herein is meant in a broad sense and includes immunoglobulin or antibody molecules including polyclonal antibodies, monoclonal antibodies including murine, human, humanized and chimeric monoclonal antibodies and antibody fragments, such as ScFv or hexabodies (PLOS Biology DOI:10.1371/journal.pbio.1002344 Jan. 6, 2016, which is hereby incorporated by reference in its entirety).

The term "humanized antibody", "engineered antibody", "human framework adapted", and "HFA" as used herein, is intended to include antibodies having variable region frameworks derived from sequences of human origin. Furthermore, if the antibody contains a constant region, the constant region can be derived from such human sequences, e.g., human germline sequences, or naturally occurring (e.g., allotypes) or mutated versions of human germline sequences. The humanized antibodies may include amino acid residues not encoded by human sequences (e.g., mutations introduced by random or site-specific mutagenesis in vitro or by somatic mutation in vivo).

In general, antibodies are proteins or polypeptides that exhibit binding specificity to a specific antigen. Intact antibodies are heterotetrameric proteins, composed of two light chains and two heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragment" means a portion of an intact antibody, generally the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies. In some embodiments, the antibody can be a single-chain variable fragment (scFv) antibody.

In some embodiments, the nucleic acid molecule encoding MAGE-A2 comprises:

```
                                               (SEQ ID NO: 2)
ATGCCGCTCGAACAGAGGAGCCAGCACTGTAAACCAGAAGAAGGACT

CGAAGCGAGGGGGAAGCGTTGGGGTTGGTAGGTGCTCAAGCACCAG

CAACTGAGGAACAGCAAACTGCGAGTTCTTCTTCCACATTGGTGGAAG

TTACTCTTGGGGAGGTTCCCGCTGCGGACAGTCCCTCCCCTCCACATTC

CCCCCAGGGTGCAAGTTCCTTTAGCACCACAATCAACTACACCCTGTG

GCGACAGTCAGATGAGGGAAGTTCTAATCAAGAAGAAGAGGGGCCAC

GCATGTTTCCCGACCTCGAGTCTGAGTTCCAAGCCGCTATAAGCAGGA

AGATGGTTGAGTTGGTTCATTTTCTGCTCCTCAAGTATCGAGCCAGGG

AGCCGGTCACAAAGGCAGAAATGCTGGAGAGTGTCCTCAGAAATTGC

CAGGACTTCTTTCCCGTGATCTTCAGCAAAGCCTCCGAGTACTTGCAG

CTGGTCTTTGGCATCGAGGTGGTGGAAGTGGTCCCCATCAGCCACTTA
```

```
TACATCCTTGTCACCTGCCTGGGCCTCTCCTACGATGGCCTGCTGGGCG

ACAATCAGGTCATGCCCAAGACAGGCCTCCTGATAATCGTCCTGGCCA

TAATCGCAATAGAGGGCGACTGTGCCCCTGAGGAGAAAATCTGGGAG

GAGCTGAGTATGTTGGAGGTGTTTGAGGGGAGGGAGGACAGTGTCTTC

GCACATCCCAGGAAGCTGCTCATGCAAGACCTGGTGCAGGAAAACTA

CCTGGAGTACCGGCAGGTGCCTGGTAGAGACCCAGCCTGTTATGAATT

TCTGTGGGGACCAAGAGCACTTATCGATACTAGTTATGTGAAAGTCCT

GCACCATACACTAAAGATCGGTGGAGAACCTCACATTTCCTACCCACC

CCTGCATGAACGGGCTTTGAGAGAGGGAGAAGAG
```

In some embodiments, the nucleic acid sequence encodes a protein of MAGE-A2 comprising the sequence of

```
                                        (SEQ ID NO: 3)
MPLEQRSQHCKPEEGLEARGEALGLVGAQAPATEEQQTASSSSTLVEVTL

GEVPAADSPSPPHSPQGASSFSTTINYTLWRQSDEGSSNQEEEGPRMFPD

LESEFQAAISRKMVELVHFLLLKYRAREPVTKAEMLESVLRNCQDFFPVI

FSKASEYLQLVFGIEVVEVVPISHLYILVTCLGLSYDGLLGDNQVMPKTG

LLIIVLAIIAIEGDCAPEEKIWEELSMLEVFEGREDSVFAHPRKLLMQDL

VQENYLEYRQVPGRDPACYEFLWGPRALIDTSYVKVLHHTLKIGGEPHIS

YPPLHERALREGEE
```

In some embodiments, the nucleic acid molecule encoding MAGE-A4 comprises:

```
                                        (SEQ ID NO: 4)
atgtcttctgagcagaagagtcagcactgcaagcctgaggaaggcgttga ggcccaagaagaggccctgggcctggtgggtgcacaggctcctactactg aggagcaggaggctgctgtctcctcctcctctcctctggtccctggcacc ctggaggaagtgcctgctgctgagtcagcaggtcctccccagagtcctca gggagcctctgccttacccactaccatcagcttcacttgctggaggcaac ccaatgagggttccagcagccaagaagaggaggggccaagcacctcgcct gacgcagagtecttgttccgagaagcactcagtaacaaggtggatgagtt ggctcatificttgctccgcaagtatcgagccaaggagctggtcacaaagg cagaaatgctggagagagtcatcaaaaattacaagcgctgctttcctgtg atcttcggcaaagcctccgagtccctgaagatgatctttggcattgacgt gaaggaagtggaccccgccagcaacacctacacccttgtcacctgcctgg gcctttcctatgatggcctgctgggtaataatcagatctttcccaagaca ggccttctgataatcgtcctgggcacaattgcaatggagggcgacagcgc ctctgaggagaaatctggaggagctgggtgtgatggggtgtatgatg ggagggagcacactgtctatgggagcccaggaaactgctcacccaagat tgggtgcaggaaaactacctggagtaccggcaggtacccggcagtaatcc
```

```
                                        -continued
tgcgcgctatgagttcctgtggggtccaagggctctggctgaaaccagct atgtgaaagtectggagcatgtggtcagggtcaatgcaagagttcgcatt gcctacccatccctgcgtgaagcagctttgttagaggaggaagagggagt ctga
```

In some embodiments, the nucleic acid molecule encodes a protein of MAGE-A4 comprising the sequence of:

```
                                        (SEQ ID NO: 5)
MSSEQKSQHCKPEEGVEAQEEALGLVGAQAPTTEEQEAAVSSSSPLVPGT

LEEVPAAESAGPPQSPQGASALPTTISFTCWRQPNEGSSSQEEEGPSTSP

DAESLFREALSNKVDELAHFLLRKYRAKELVTKAEMLERVIKNYKRCFPV

IFGKASESLKMIFGIDVKEVDPASNTYTLVTCLGLSYDGLLGNNQIFPKT

GLLIIVLGTIAMEGDSASEEEIWEELGVMGVYDGREHTVYGEPRKLLTQD

WVQENYLEYRQVPGSNPARYEFLWGPRALAETSYVKVLEHVVRVNARVRI

AYPSLREAALLEEEEGV
```

As is known to the skilled artisan, a peptide having a specific amino acid sequence can be encoded by different nucleic acid molecules because of the fact that the genetic code is degenerate. In some embodiments, the nucleic acid molecule's sequence is optimized. The sequence can be optimized based upon codon usage and frequency depending upon the cell type that is being used or the subject that is being administered the nucleic acid molecule. Codon optimization can be useful to maximize protein expression. This can be done by optimizing the codon usage of mRNA sequences for mammalian cells. For example, changing the immunogen gene sequences encoding infectious target proteins used within nucleic acid molecule can be used to increase expression and the expressed protein immunogenicity. Methods of optimizing codon usage are known. Additionally, the nucleic acid molecules provided for herein may have stop codons in the sequence. One of skill in the art would understand that the stop codons could be replaced by degenerate stop codons. Stop codons are known to be U(T)AA, U(T)AG, and U(T)GA.

Thus, the nucleic acid sequences shown in the table above are simply for illustration purposes only and not intended to be limiting to those that encode for the relevant amino acid sequence of the target protein. Additionally, in some embodiments, less than the full length of the target protein is used. In some embodiments, at least 5, 10, 15, or 20 amino acid residues, independently, from the N- and/or C-terminus are not encoded for by the nucleic acid molecule. In some embodiments, the target protein is larger than the fragment of the target protein that is encoded for by the nucleic acid molecule.

In some embodiments, the proteins encoded by the nucleic acid molecules provided herein comprise conservative substitutions. Conservative substitutions are known to the skilled artisan.

In some embodiments, the nucleic acid molecule comprises a different nucleic acid molecule comprising a nucleic sequence that encodes for a fragment of the target protein. In some embodiments, the fragment comprises about 7 to about 25 residues of the target protein. In some embodiments, the fragment comprises about 7 to about 20, about 7 to about 18, about 7 to about 15, about 7 to about 13, about 7 to about 12, about 7 to about 11, about 7 to about 9, about 8 to about 25, about 8 to about 20, about 8 to about 18, about 8 to about 15, about 8 to about 13, about 8 to about 12, about 8 to about 11, about 8 to about 9, about 9 to about 25, about 9 to about 20, about 9 to about 18, about 9 to about 15, about 9 to about 13, about 9 to about 12, about 9 to about 11 residues of the target protein, and the like. In some embodiments, the fragment is, or is about, 9, 10, 11, 12, 13, 14, 15, 16, 17, 18, 29, 20, 21, 22, 23, 24, or 25 amino acid residues in length.

In some embodiments, the fragment of the target protein and/or the target protein itself elicits an immunogenic response by MHC I or MHC II CD8+ immune cells or T-cytotoxic lymphocytes. In some embodiments, the fragment of the target protein is represented by the amino acid sequence in the following table:

| Target Fragment of Protein | Amino Acid Sequence of fragment (SEQ ID NO) | Non-limiting Nucleic Acid Sequences encoding the amino acid sequence (SEQ ID NO) |
|---|---|---|
| MAGE-A2 Fragment | KMVELVHFL (SEQ ID NO: 6) | AAAATGGTTGAACTTGTTCATTTTCTT (SEQ ID NO: 7) |
| MAGE-A4 Fragment | KVDELAHFL (SEQ ID NO: 8) | AAGGTGGATGAGTTGGCTCATTTTCTG (SEQ ID NO: 9) |

The fragments can also be encoded by other nucleic acid molecules that comprise a sequence that encodes the fragment. The nucleic acid sequence represented in the table is merely for illustrative purposes only and should not be construed as limiting.

In some embodiments, the nucleic acid sequence comprises a sequence encoding a linker such as, but not limited to a glycine-serine or glycine-alanine linker. In some embodiments, the glycine-serine linker comprises the sequence of GGGGS (SEQ ID NO: 13). The linker can also comprise repeats of this sequence. In some embodiments, the linker comprises 1, 2, 3, 4, 5, 6, 7, 8, 9 or 10 GGGGS repeats. In some embodiments, the glycine-alanine linker comprises the sequence of GGGGA (SEQ ID NO: 10). The linker can also comprise repeats of this sequence. In some embodiments, the linker comprises 1, 2, 3, 4, 5, 6, 7, 8, 9 or 10 GGGGA (SEQ ID NO: 10) repeats. The linker can also comprise a mixture of the linker sequences. Thus, in some embodiments, the linker could comprise a sequence of GGGGSGGGGAGGGGS (SEQ ID NO: 11), and the like. Other peptide linkers can also be used. In some embodiments, the glycine-serine linker comprises a sequence of: GGSGS (SEQ ID NO: 12) and multiple repeats thereof. There can be 1, 2, 3, 4, 5, 6, 7, 8, 9, or 10 repeats of any of the linkers provided herein. The linkers can also be mixed with one another. In some embodiments, the nucleic acid molecules provided for herein do not contain or do not comprise (e.g. free of) a sequence encoding a linker.

In some embodiments, the nucleic acid molecule encodes ubiquitin as a single ubiquitin protein or a chain of 2 or more ubiquitin proteins. In some embodiments, the sequence encoding the ubiquitin is selected from a sequence encoding UBB, UBC, UBA52, and RPS27A. The encoded ubiquitin can be a homogenous ubiquitin chain or a heterogeneous ubiquitin chain comprising different ubiquitin molecules. Examples of such sequences would include, but are not limited to those in the following table:

| Ubiquitin Protein Name | Amino Acid Sequence (SEQ ID NO) | Non-limiting Nucleic Acid Sequences encoding the amino acid sequence (SEQ ID NO) |
|---|---|---|
| UBB | MQIFVKTLTGKTITLEVEPSDTIE NVKAKIQDKEGIPPDQQRLIFAG KQLEDGRTLSDYNIQKESTLHLV LRLRGG (SEQ ID NO: 14) | ATGCAGATCTTCGTGAAGACGTTAACC GGTAAAACCATAACTCTCGAAGTTGAA CCATCCGATACCATCGAAAACGTTAAG GCTAAAATTCAAGACAAGGAAGGCATT CCACCTGATCAACAAAGATTGATCTTT GCCGGTAAGCAGCTGGAGGACGGTAG AACGCTGTCTGATTACAACATTCAGAA GGAGTCGACCTTACATCTTGTCTTAAG ACTAAGAGGTGGT (SEQ ID NO: 15) |
| UBC | MQIFVKTLTGKTITLEVEPSDTIENVKAKI QDKEGIPPDQQRLIFAGKQLEDGRTLSDYN IQKESTLHLVLRLRGGMQIFVKTLTGKTIT LEVEPSDTIENVKAKIQDKEGIPPDQQRLI FAGKQLEDGRTLSDYNIQKESTLHLVLRLR GGMQIFVKTLTGKTITLEVEPSDTIENVKA KIQDKEGIPPDQQRLIFAGKQLEDGRTLSD YNIQKESTLHLVLRLRGGMQIFVKTLTGKT ITLEVEPSDTIENVKAKIQDKEGIPPDQQR LIFAGKQLEDGRTLSDYNIQKESTLHLVLR LRGGMQIFVKTLTGKTITLEVEPSDTIENV KAKIQDKEGIPPDQQRLIFAGKQLEDGRTL SDYNIQKESTLHLVLRLRGGMQIFVKTLTG KTITLEVEPSDTIENVKAKIQDKEGIPPDQ QRLIFAGKQLEDGRTLSDYNIQKESTLHLV LRLRGGMQIFVKTLTGKTITLEVEPSDTIE NVKAKIQDKEGIPPDQQRLIFAGKQLEDGR TLSDYNIQKESTLHLVLRLRGGMQIFVKTL TGKTITLEVEPSDTIENVKAKIQDKEGIPP DQQRLIFAGKQLEDGRTLSDYNIQKESTLH LVLRLRGGMQIFVKTLTGKTITLEVEPSDT IENVKAKIQDKEGIPPDQQRLIFAGKQLED GRTLSDYNIQKESTLHLVLRLRGGV (SEQ ID NO: 16) | |

| Ubiquitin Protein Name | Amino Acid Sequence (SEQ ID NO) | Non-limiting Nucleic Acid Sequences encoding the amino acid sequence (SEQ ID NO) |
|---|---|---|
| UBA52 | MQIFVKTLTGKTITLEVEPSDTIENVKAKI QDKEGIPPDQQRLIFAGKQLEDGRTLSDYN IQKESTLHLVLRLRGGIIEPSLRQLAQKYN CDKMICRKCYARLHPRAVNCRKKKCGHTNN LRPKKKVK (SEQ ID NO: 17) | |
| RPS27A | MQIFVKTLTGKTITLEVEPSDTIENVKAKI QDKEGIPPDQQRLIFAGKQLEDGRTLSDYN IQKESTLHLVLRLRGGAKKRKKKSYTTPKK NKHKRKKVKLAVLKYYKVDENGKISRLRRE CPSDECGAGVFMASHFDRHYCGKCCLTYCF NKPEDK (SEQ ID NO: 18) | |

In some embodiments, the nucleic acid molecules provided herein do not comprise (e.g. are free of) a sequence that encode a ubiquitin protein.

In some embodiments, the nucleic acid sequence comprises a sequence encoding a nuclear localization signal. A non-limiting example of a nuclear localization signal encoded by a nucleotide sequence is Element 1, which can be encoded by a nucleic acid molecule comprising the sequence of:

(SEQ ID NO: 19)
CACAATTCCACACATGTGTGAAATTGTTATCCGCTCACAATTCCACAC

ATGTGTGAAATTGTTATCCGCTCACAATTCCACACACGTGCTAAAA

CTTCATTTT

In some embodiments, a nucleic acid molecule is provided that encodes a protein that comprises a full length protein, a glycine-serine linker, a ubiquitin protein, and a fragment of the full length protein. In some embodiments, the nucleic acid molecule encoding the fragment is not included in the nucleic acid molecule or plasmid. If there is no fragment of the target molecule, the sequence encoding the ubiquitin protein is not necessary. Thus, in some embodiments, the nucleic acid molecule encoding the ubiquitin protein is not present, or put another way, the nucleic acid molecule is free of a sequence encoding a ubiquitin protein.

Thus, in some embodiments, a nucleic acid molecule is provided that encodes a protein that comprises a full length protein and a NLS signal without a molecule that encodes for a linker sequence, a ubiquitin protein or a fragment of the protein. The nucleic acid molecule can be a plasmid.

Figure 2:
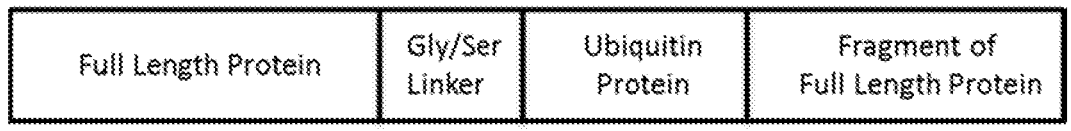
FIG. 2 illustrates a non-limiting embodiments of a nucleic acid molecule, such as a plasmid, as described herein.
Figure 3:
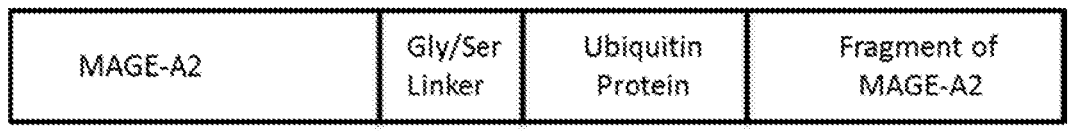
FIG. 3 illustrates a non-limiting embodiments of a nucleic acid molecule, such as a plasmid, as described herein.
Figure 4:
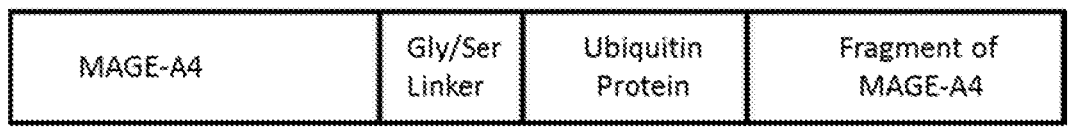
FIG. 4 illustrates a non-limiting embodiments of a nucleic acid molecule, such as a plasmid, as described herein.

Examples of the fragments are provided herein and can be about 7 to about 25 amino acids in length or as otherwise described herein. A non-limiting example of such protein can be illustrated as shown in FIG. 2. Other non-limiting examples can be illustrated as shown in FIG. 3 and FIG. 4:

In some embodiments, the Gly/Ser linker of these embodiments is as provided herein, including but not limited to, GGGGS, GGGGA, or GGSGS. In some embodiments, the ubiquitin protein is UBB, or SEQ ID NO: 14. In some embodiments, the fragment is SEQ ID NO: 6 or 8.

In some embodiments, the nucleic acid molecules provided for herein do not contain or do not comprise (e.g. free of) a sequence encoding a linker.

The other elements, which may or may not be present, of the nucleic acid molecule can be operably linked to the sequence encoding the protein.

In some embodiments, a pharmaceutical composition is provided that comprises the nucleic acid molecules described herein such as, but not limited to, a nucleic acid molecule comprising a sequence encoding a constitutive promoter, a sequence encoding an amino acid sequence of a target protein, a sequence encoding an amino acid sequence of a linker, a sequence encoding an amino acid sequence of ubiquitin, a sequence encoding at least 7 amino acid residue peptide fragment of the target protein, and a sequence encoding a nuclear localization signal, wherein the sequences are operatively connected to one another and the sequences of b), c), d), and e) are operatively connected to one another to encode a protein comprising the amino acid sequence of the full-length protein; the amino acid sequence of the linker, the amino acid sequence of ubiquitin, and at least 7 amino acid residues of the target protein. Other fragments sizes are provided for herein.

Also provided herein are the proteins or peptides encoded by the nucleic acid molecules described herein.

In some embodiments, nucleic acid molecules are provided, wherein the nucleic acid molecule comprises a polynucleotide encoding a promoter. In some embodiments, the promoter is a constitutive promoter. Non-limiting examples of constitutive promoters that can be used are provided for herein. In some embodiments, the nucleic acid molecule comprises a polynucleotide encoding a target molecule or a target protein. Examples of the target molecules and proteins are provided for herein. These examples are for illustrative purposes only and are intended to be non-limiting. The target molecule or protein can be any molecule or protein encoded for by a nucleic acid molecule that one chooses to be encoded for by the nucleic acid molecule. In some embodiments, the nucleic acid molecule comprises a polynucleotide encoding a linker. Examples of linkers are provided for herein. For example, the linker can be any peptide linker that can be encoded for by a nucleic acid molecule. In some embodiments, the nucleic acid molecule comprises a polynucleotide encoding a ubiquitin. Examples of linkers are provided for herein. In some embodiments, the nucleic acid molecule comprises a polynucleotide encoding a fragment of the target protein. Various fragment sizes are provided for herein. In some embodiments, the fragment is about 7 to about 25 amino acid residues of the target protein. In some embodiments, the nucleic acid molecule comprises a polynucleotide encoding a nuclear localization signal (NLS). In some embodiments, the NLS does not encode for a protein or tag that gets expressed. Instead, the NLS can be a nucleic acid molecule that is recognized by the cell and ensure that the nucleic molecule comprising the NLS is present (e.g. transported to) in the nucleus. The elements provided for herein can be operatively connected to one another. If all of the elements are present the nucleic acid molecule can encode a protein comprising the amino acid sequence of the full-length protein; the amino acid sequence of the linker, the amino acid sequence of ubiquitin, and a fragment of the target protein.

The nucleic acid molecules provided for herein can be provided as a single molecule, for example as a plasmid. In some embodiments, each element is encoded by a single polynucleotide sequence (or double stranded molecule, such as, but not limited to a plasmid) as opposed to distinct nucleotide molecules encoding for different elements. The use of a single molecule, such as a plasmid, permits the user to efficiently introduce the target molecule or target protein into the relevant cell or cellular environment.

In some embodiments, the nucleic acid molecules provided herein comprise one or more of a polynucleotide encoding a constitutive promoter; a polynucleotide encoding an a target molecule, which can also be referred to as a molecule of interest; and a polynucleotide encoding a nuclear localization signal; wherein the sequences can be, or are, operatively connected one another. In some embodiments, the nucleic acid molecules provided herein comprise a polynucleotide encoding a constitutive promoter; a polynucleotide encoding an a target molecule, which can also be referred to as a molecule of interest; and a polynucleotide encoding a nuclear localization signal; wherein the sequences are operatively connected one another. The molecule of interest (target molecule) can be any molecule that can be encoded by the nucleic acid molecule. For example, the target molecule can be a chimeric antigen receptor (CAR) that can be expressed in a T-cell or other type of cell and function in the T-cell. Thus, the nucleic acid molecule, which can be in the form of a plasmid, can be used to deliver a target molecule to a cell of interest. In some embodiments, the cell is an immune cell, such as a T-cell, dendritic cell, NK cell, a TIL, a MIL, and the like.

In some embodiments, the nucleic acid molecule is used to deliver a target molecule that can be expressed in a cell. Thus, the nucleic acid molecule, which can be a plasmid, can be used to express a protein or nucleic acid molecule in a cell. The target molecule can be a nucleic acid molecule that encodes for a protein, an antisense nucleic acid molecule, a siRNA molecule, a microRNA, an antibody, a receptor, or any other type of molecule that can be encoded for by a nucleic acid molecule, such as those described herein. Other examples of products that can be encoded for are insulin, hormones, gene products, and the like. The specific structure of the gene product is not necessarily critical, but instead shows that various embodiments that the nucleic acid molecules, such as a plasmid, can be used for. In some embodiments, the target molecule is an antibody that can treat cancers, such as antibodies that bind to PD-1, PD-L1, BSMA, and the like. Examples of such antibodies include, but are not limited to, pembrolizumab, nivolumab, and the like. Examples of CARs that can be used include those that are comprise an extracellular region that bind to PD-1, PD-L1, BSMA, PSMA, and the like. In some embodiments, the CAR comprises a CD19 extracellular binding domain. In some embodiments, the CAR comprises a 4-1BB intracellular region In some embodiments, the CAR comprises a CD3ζ intracellular signaling domain. In some embodiments, the CAR comprises a CD28 intracellular domain. In some embodiments, the transmembrane domain of the CAR is a CD3ζ transmembrane domain or a CD28 transmembrane domain. As described herein, in some embodiments, the nucleic acid molecule, e.g. plasmid, is a non-integrating nucleic acid molecule.

In some embodiments, the nucleic acid molecules provided for herein are administered to a subject and taken up by the cells. In some embodiments, the cells are treated with the nucleic acid molecule (e.g. plasmid) ex-vivo and then administered back to a subject to express the molecules in vivo. In some embodiments, the nucleic acid molecules is complexed with nanoparticles to deliver the nucleic acid molecule to a specific cell type. For example, the nucleic acid molecule can be encapsulated or complexed with a lipid nanoparticle, a polymer nanoparticle, liposome, a neutral liposome, a biodegradable polymer matrix (e.g. hydrogel), and the like. Example of nanoparticles are described in Xiao et al., Molecular Therapy: Methods & Clinical Development Vol. 12 Mar. 2019, pp. 1-18, which is hereby incorporated by reference in its entirety. Examples of polymers that can be used include, but are not limited to, The research most focuses on polyetherimide (PEI), Lactosylated polylysine (PLL), polyacrylic acid (PAA), poly(aliphatic ester) (PAE), and poly(N,N-dimethylaminoethyl methacrylate) (PD-MAEMA). These polymers can be modified by chemical modification or can be free of modifications. Other polymers include, but are not limited to, chitosan (e.g. cationic chitosan), Poly(ethyleneglycol)-modified chitosan (PEG-CS), carboxymethyl dextran (CMD)-chitosan, gelatin (e.g. cationic gelatin), dextran (e.g. Cationic dextran), cellulose (e.g. cationic cellulose), cyclodextrin (e.g. cationic cyclodextrin).

In some embodiments, the nucleic acid molecule is not encapsulated with a carrier or nanoparticle. In some embodiments, the pharmaceutical composition is free of a nanoparticle that encapsulates the nucleic acid molecule.

As described herein, the nucleic acid molecule can comprise a promoter, such as a constitute promoter. Examples of constitutive promoters include, but are not limited to EF-1, SV40, Rous Sarcoma virus, and Mason-Pfizer monkey virus-CTE. In some embodiments, the promoter is EF-1. In some embodiments, the promoter is SV40. In some embodiments, the promoter is RSV. In some embodiments, the promoter is the Mason-Pfizer monkey virus-CTE.

The nucleic acid molecules can also further comprise a nucleic acid sequence that encodes for one or more adjuvants. In some embodiments, the adjuvant is IL-12. In some embodiments, the nucleic acid molecule encodes one or more of the group consisting of: anti-CD40 antibody, GM-CSF, bevacizumab, interferon-alpha, interferon-beta, poly-(I:C) and derivatives, RNA interleukin (IL)-1, IL-2, IL-4, IL-7, IL-12, IL-13, IL-15, IL-21, and IL-23, and the like.

In some embodiments, the nucleic acid molecules provided for herein can comprise a sequence encoding a nuclear localization signal (NLS). In some embodiments, the NLS is element 1. In some embodiments, the sequence is as shown SEQ ID NO: 19.

For the avoidance of doubt, any of the nucleic acid molecules provided for herein can be a plasmid or other type of circular DNA sequence, such that it can be used to express its products in a cell.

In some embodiments, pharmaceutical compositions comprising the nucleic acid molecules described herein are provided. Examples of pharmaceutical compositions are provided for herein.

In some embodiments, methods of delivering a molecule to a cell are provided. In some embodiments, the methods comprise contacting a cell with a nucleic acid molecule as provided for herein into a cell of the subject or into the subject and said nucleic acid sequence is taken up by the cell in the subject. The nucleic acid molecule is then expressed and the target molecules or other expression cassettes are expressed in the cell. In some embodiments, the nucleic acid sequence is introduced into the cell or subject by electroporation, injection, sonication, transfection, transduction, gene guns, encompassed by nanoparticles, lipoparticles, or other modes of administration suitable for introducing a nucleic molecule into a subject or cell. In some embodiments, the cell or tissue that the nucleic acid molecule is delivered to is skin, muscle, breast, lung, pancreas, brain, ovarian, uterine, endometrial, colon, prostate, esophageal, gum, tongue, throat, or kidney tissue or cell.

These examples are non-limiting and the molecules and compositions provided for herein can be used in any tissue or cell type desired by the user.

In some embodiments, the compositions and molecules described herein can be used to treat cancer. Examples of cancers that can be treated include, but are not limited to, brain, breast, lung, ovarian, endometrial, colon, lung, skin (e.g. melanoma), and the like.

Pharmaceutical compositions described herein can further comprise a pharmaceutically acceptable carrier or diluent. In some embodiments, the pharmaceutical compositions comprise about 1 ng to about 10,000 µg of the nucleic acid molecule. The pharmaceutical compositions can be formulated according to the mode of administration to be used. One having ordinary skill in the art can readily formulate a pharmaceutical composition that comprises a genetic construct or nucleic acid molecule as described herein. In cases where intramuscular injection is the chosen mode of administration, an isotonic formulation can be used. In some embodiments, additives for isotonicity can include sodium chloride, dextrose, mannitol, sorbitol, lactose, and the like. In some cases, isotonic solutions such as phosphate buffered saline are used. In some embodiments, the pharmaceutical composition comprises a stabilizer. Examples of stabilizers include, but are not limited to, gelatin and albumin. The pharmaceutical preparations can be provided as sterile and pyrogen free.

In some embodiments, methods of inducing an immune response against a target protein in a subject are provided. In some embodiments, the methods comprise introducing the nucleic acid molecules described herein into the subject. In some embodiments, the nucleic acid molecule is introduced in a cell of the subject. The nucleic acid molecule can also be taken up by the cell. Once inside the cell the cell's machinery can be used to express the target protein and the construct that is encoded for by the nucleic acid molecule. In some embodiments, the nucleic acid molecule is as described herein. The method of introduction or administration can be any method, including the methods described herein. In some embodiments, the nucleic acid molecule is introduced by electroporation or injection. In some embodiments, the nucleic acid molecule is introduced into, or administered to, the subject by sonication, transfection, transduction, gene guns, nanoparticles, lipoparticles, or other modes of administration suitable for introducing a nucleic molecule into a subject or cell and the like.

In some embodiments, bupivacaine or other similar adjuvant is used to help facilitate the induction of an immune response.

In some embodiments, the nucleic acid molecule is administered to a tissue of the subject. In some embodiments, the tissue is skin, muscle, liver, fat, and the like.

In some embodiments, methods of treating cancer are provided. In some embodiments, the methods of treating cancer in a subject introducing, or administering, a nucleic acid molecule described herein to the subject. In some embodiments, the nucleic acid molecule is introduced directly into a cell. In some embodiments, the nucleic acid molecule is taken up by the cell and expressed in the cell. In some embodiments, the target protein and the fragment of the target protein is a protein that is overexpressed, or specifically expressed, in a cancer cell. In some embodiments, the nucleic acid molecule is administered by electroporation, injection, sonication, transfection, transduction, and the like. In some embodiments, the nucleic acid molecule is administered to the skin, muscle or other tissue of the subject. In some embodiments, the cancer is lung cancer, breast cancer, uterine cancer, prostate cancer, ovarian cancer, colorectal cancer, melanoma, myeloma, brain cancer, colon cancer, pancreatic cancer, and the like. In some embodiments, the cancer is triple negative breast cancer, uterine cancer, prostate cancer, ovarian cancer, or colorectal cancer.

In some embodiments, methods of treating an infectious agent or an infection in a subject are provided. In some embodiments, the methods comprise introducing/administering the nucleic acid molecules described herein to the subject. In some embodiments, the nucleic acid molecule is administered directly into a cell of the subject. As described throughout, the nucleic acid molecule can be taken up by the cell and expressed in the cell. Without being bound by any particular theory, when the nucleic acid molecule is expressed the subject's immune response will recognize the target protein and the fragment of the target protein as foreign and an immune response will be generated. The generated immune response can treat or prevent the infection. In some embodiments, the generated immune response can treat or prevent the infectious agent from causing a disease or will inhibit the growth of the infectious agent to ameliorate symptoms of the infection. The methods of administration can be any of the methods described herein. In some embodiments, the nucleic acid molecule can be administered to the skin, muscle, fat, kidney, or other tissue of the subject. In some embodiments, the nucleic acid molecule is administered to the mucosa of the subject. In some embodiments, the method of treating an infectious agent in a subject comprises introducing the nucleic acid molecule into a cell of the subject and said nucleic acid sequence is taken up by the cell in the subject, wherein the protein is a protein that is expressed by the infectious agent. In some embodiments, the nucleic acid molecule is introduced into the subject or the cell by electroporation, injection, sonication, transfection, and transduction.

In some embodiments, the target protein is a HIV or influenza protein, such as Gp120, Gag, Nef, Tat, hemagglutinin (HA), neuraminidase (NA), and the like.

In some embodiments, the subject can also be treated with an antibody that targets a protein involved in tumorigenesis. For example, in some embodiments, the subject is administered an anti-PD-L1, anti-PD-1, and/or anti-CTL4 antibody with the nucleic acid molecules described herein. The antibody can be administered before, after or concurrently with the nucleic acid molecules provided herein.

In some embodiments, a cell comprising the nucleic acid molecules provided for herein are provided. In some embodiments, the cell is an isolated cell. In some embodiments, the cell is ex-vivo and not in a subject. The cell can be any cell type, such as a T-cell, a muscle cell, a skin cell, a brain cell, and the like.

The following examples are illustrative, but not limiting, of the compositions and methods described herein. Other suitable modifications and adaptations known to those skilled in the art are within the scope of the following embodiments.

Example 1

A DNA element called Nuclear Localization Domain, which was Element 1, contains a sequence that mimics the trafficking of viruses inside of cells, which can aid in the localization of the DNA to the cell nucleus as well as encoded mRNA export from the nucleus.

Experiments have shown that when these elements were introduced into the sequence of a standard Green Fluorescent Protein (GFP)-expressing plasmid DNA expression vector and transfected into mammalian cells using commercially available cationic lipid transfection reagents (i.e. Lipofectmine), they can enhance GFP expression by several fold as illustrated by FIG. 1.

A nucleic acid molecule, such as those provided herein, were designed to be a DNA-based delivery system that can directly enhance the immune system via CD8+ and CD4+ lymphocytes that can be used to reduce tumor load and/or prevent tumor recurrence. Pre-clinical studies of Optimized SMART Plasmid DNAs along with anti-PD-L1 (e.g. Atezolizumab) and/or anti-CTL4 (e.g. Ipilimumab) is undergoing testing to demonstrate the potential to initiate a systemic immune response that can lead to decreased toxicities of current chemotherapies. PD-L1 and/or CTL4 have been found to be potential tumor immunotherapy target using antibodies.

In addition, SMART Plasmid DNA in conjunction with anti-PD-L1 and/or anti-CTL4 could be used as a standalone treatment for many tumors that express the protein antigens, such as, MAGE-A.

Through prior studies, specific regions of viral proteins, such as, the lentiviral integrase protein, is capable of enhancing nuclear transport of viral DNA SMART Plasmid DNA incorporates portions of such viral proteins into Element 1, which enhances viral DNA import into the nucleus and begin the process of translating the target sequences.

The DNA localization properties of Element 1 in SMART Plasmid DNA are magnified when used in combination with viral proteins added exogenously.

The sequence of the plasmid DNA elements as well as their structural orientation within the plasmid leads to enhanced protein expression in vitro.

Without being bound to any particular theory, it is thought that the mechanism of action for these elements provides a 3-dimensional structural element that allows the DNA to more efficiently be transported through the mammalian cell nuclear pore via enhanced passive transport or to be actively transported through the pore by interacting with molecules that shuttle to the nucleus regularly. In addition, an Element 1 NLS contained within the nucleic acid molecule can localize transcribed messenger RNA from the nucleus to the cytoplasm, where these mRNA molecules can be translated into protein, for example, for a therapeutic benefit.

The fully synthetic method for producing lentivirus-like vector particles for mammalian cell transduction is a powerful template in which to build an immunotherapy for the treatment of antigen expressing tumors and other disease entities. It represents a major technological advance in gene delivery technology, transfection, and immunotherapy.

The DNA sequences can also be represented in a circular plasmid and encode a target protein that is MAGE A-2. The plasmid comprises the sequences of: EF-1 promoter nucleotide sequence, MAGE-A2 full length nucleotide sequence, Glycine-Serine linker nucleotide sequence, Ubiquitin nucleotide sequence, MAGE-A2 9mer peptide nucleotide sequence, and Element 1 (nuclear localization domain) nucleotide sequence. The plasmid can also comprises the sequence of a Kanamcin/Neomycin nucleotide sequence region, and a ColE1 origin nucleotide sequence. A non-limiting example of the MAGE A2 9-mer plasmid sequence is provided as SEQ ID NO: 20 below:

MAGE A2 9-mer plasmid sequence:

(SEQ ID NO. 20)

```
GACTCTTCGCGATTATCGCCGAATTCACGCGTCGTGAGGCTCCTGCAGG
GCCGACTAGTGGAGCCGAGAGTAATTCATACAAAAGGAGGGATCGCCTT
CGCAAGGGGAGAGCCCAGGGACCGTCCCTAAATTCTCACAGACCCAAAT
CCCTGTAGCCGCCCCACGACAGCGCGAGGAGCATCCGCCCAGGGCTGAG
CGCGGGTAGATCAGAGCACACAAGCTCACAGTCCCCGGCGGTGGGGGA
GGGGCGCGCTGAGCGGGGGCCAGGGAGCTGGCGCGGGGCAAACTGGGAA
AGTGGTGTCGTGTGCTGGCTCCGCCCTCTTCCCGAGGGTGGGGGAGAAC
GGTATATAAGTGCGGTAGTCGCCTTGGACGTTCTTTTTCGCAACGGGTT
TGCCGTCAGAACGCAGCTGAAGCTTCGAGGGCTCGCATCTCTCCTTCAC
GCGCCCGCCGCCCTACCTGAGGCCGCCATCCACGCCGGTTGAGTCGCGT
TCTGCCGCCTCCCGCCTGTGGTGCCTCCTGAACTGCGTCCGCCGTCTAG
GTAAGTTTAAAGCTCAGGTCGAGACCGGGCCTTTGTCCGGCGCTCCCTT
GGAGCCTACCTAGACTCAGCCGGCTCTCCACGCTTTGCCTGACCCTGCT
TGCTCAACTCTACGTCTTTGTTTCGTTTTCTGTTCTGCGCCGTTACAGA
TCCAAGCCAGCTAGCGTTTAAACTTGCCGCCACCATGCCGCTCGAACAG
AGGAGCCAGCACTGTAAACCAGAAGAAGGACTCGAAGCGAGGGGGGAAG
CGTTGGGGTTGGTAGGTGCTCAAGCACCAGCAACTGAGGAACAGCAAAC
TGCGAGTTCTTCTTCCACATTGGTGGAAGTTACTCTTGGGGAGGTTCCC
GCTGCGGACAGTCCCTCCCCTCCACATTCCCCCCAGGGTGCAAGTTCCT
TTAGCACCACAATCAACTACACCCTGTGGCGACAGTCAGATGAGGGAAG
TTCTAATCAAGAAGAAGAGGGGCCACGCATGTTTCCCGACCTCGAGTCT
GAGTTCCAAGCCGCTATAAGCAGGAAGATGGTTGAGTTGGTTCATTTTC
TGCTCCTCAAGTATCGAGCCAGGGAGCCGGTCACAAAGGCAGAAATGCT
GGAGAGTGTCCTCAGAAATTGCCAGGACTTCTTTCCCGTGATCTTCAGC
AAAGCCTCCGAGTACTTGCAGCTGGTCTTTGGCATCGAGGTGGTGGAAG
TGGTCCCCATCAGCCACTTATACATCCTTGTCACCTGCCTGGGCCTCTC
CTACGATGGCCTGCTGGGCGACAATCAGGTCATGCCCAAGACAGGCCTC
CTGATAATCGTCCTGGCCATAATCGCAATAGAGGGCGACTGTGCCCCTG
AGGAGAAAATCTGGGAGGAGCTGAGTATGTTGGAGGTGTTTGAGGGGAG
GGAGGACAGTGTCTTCGCACATCCCAGGAAGCTGCTCATGCAAGACCTG
GTGCAGGAAAACTACCTGGAGTACCGGCAGGTGCCTGGTAGAGACCCAG
CCTGTTATGAATTTCTGTGGGACCAAGAGCACTTATCGATACTAGTTA
TGTGAAAGTCCTGCACCATACACTAAAGATCGGTGGAGAACCTCACATT
TCCTACCCACCCCTGCATGAACGGGCTTTGAGAGAGGGAGAAGAGGGTG
```

-continued

```
GTTCTGGTAGCATGCAGATCTTCGTGAAGACGTTAACCGGTAAAACCAT

AACTCTCGAAGTTGAACCATCCGATACCATCGAAAACGTTAAGGCTAAA

ATTCAAGACAAGGAAGGCATTCCACCTGATCAACAAAGATTGATCTTTG

CCGGTAAGCAGCTGGAGGACGGTAGAACGCTGTCTGATTACAACATTCA

GAAGGAGTCGACCTTACATCTTGTCTTAAGACTAAGAGGTGGTAAAATG

GTTGAACTTGTTCATTTTCTTTGACTCGAGCGCGCTGGGCCCTTTAAAC

CCGCTGATCAGCCTCGACCGTGCCTTCTAGTTGCCAGCCATCTGTTGTT

TGCCCCTCCCCCGTGCCTTCCTTGACCCTGGAAGGTGCCACTCCCACTG

TCCTTTCCTAATAAAATGAGGAAATTGCATCGCATTGTCTGAGTAGGTG

TCATTCTATTCTGGGGGTGGGGTGGGGCAGGACAGCAAGGGGGAGGAT

TGGGAAGACAATAGCAGGCATGCTGGGGATGCGGTGGGCTCTATGGCTT

CTACTGGGCGGTTTTATGGACAGCAAGCGAACCGGAATTGCCAGCTGGG

GCGCCCTCTGGTAAGGTTGGGAAGCCCTGCAAAGTAAACTGGATGGCTT

TCTCGCCGCCAAGGATCTGATGGCGCAGGGGATCAAGCTCTGATCAAGA

GACAGGATGAGGATCGTTTCGCATGATTGAACAAGATGGATTGCACGCA

GGTTCTCCGGCCGCTTGGGTGGAGAGGCTATTCGGCTATGACTGGGCAC

AACAGACAATCGGCTGCTCTGATGCCGCCGTGTTCCGGCTGTCAGCGCA

GGGGCGCCCGGTTCTTTTGTCAAGACCGACCTGTCCGGTGCCCTGAAT

GAACTGCAAGACGAGGCAGCGCGGCTATCGTGGCTGGCCACGACGGGCG

TTCCTTGCGCAGCTGTGCTCGACGTTGTCACTGAAGCGGGAAGGGACTG

GCTGCTATTGGGCGAAGTGCCGGGCAGGATCTCCTGTCATCTCACCTT

GCTCCTGCCGAGAAAGTATCCATCATGGCTGATGCAATGCGGCGGCTGC

ATACGCTTGATCCGGCTACCTGCCCATTCGACCACCAAGCGAAACATCG

CATCGAGCGAGCACGTACTCGGATGGAAGCCGGTCTTGTCGATCAGGAT

GATCTGGACGAAGAGCATCAGGGGCTCGCGCCAGCCGAACTGTTCGCCA

GGCTCAAGGCGAGCATGCCCGACGGCGAGGATCTCGTCGTGACCCATGG

CGATGCCTGCTTGCCGAATATCATGGTGGAAAATGGCCGCTTTTCTGGA

TTCATCGACTGTGGCCGGCTGGGTGTGGCGGACCGCTATCAGGACATAG

CGTTGGCTACCCGTGATATTGCTGAAGAGCTTGGCGGCGAATGGGCTGA

CCGCTTCCTCGTGCTTTACGGTATCGCCGCTCCCGATTCGCAGCGCATC

GCCTTCTATCGCCTTCTTGACGAGTTCTTCTGAATTATTAACGCTTACA

ATTTCCTGATGCGGTATTTTCTCCTTACGCATCTGTGCGGTATTTCACA

CCGCATACAGGTGGCACTTTTCGGGGAAATGTGCGCGGAACCCCTATTT

GTTTATTTTTCTAAATACATTCAAATATGTATCCGCTCATGAGACAATA

ACCCTGATAAATGCTTCAATAATAGCACGTGTGTGTGAAATTGTTATCC

GCTCACAATTCCACACATGTGTGAAATTGTTATCCGCTCACAATTCCAC

ACATGTGTGAAATTGTTATCCGCTCACAATTCCACACACACGTGCTAAA

ACTTCATTTTTAATTTAAAAGGATCTAGGTGAAGATCCTTTTTGATAAT

CTCATGACCAAAATCCCTTAACGTGAGTTTTCGTTCCACTGAGCGTCAG

ACCCCGTAGAAAAGATCAAAGGATCTTCTTGAGATCCTTTTTTTCTGCG

CGTAATCTGCTGCTTGCAAACAAAAAAACCACCGCTACCAGCGGTGGTT

TGTTTGCCGGATCAAGAGCTACCAACTCTTTTTCCGAAGGTAACTGGCT

TCAGCAGAGCGCAGATACCAAATACTGTCCTTCTAGTGTAGCCGTAGTT

AGGCCACCACTTCAAGAACTCTGTAGCACCGCCTACATACCTCGCTCTG

CTAATCCTGTTACCAGTGGCTGCTGCCAGTGGCGATAAGTCGTGTCTTA

CCGGGTTGGACTCAAGACGATAGTTACCGGATAAGGCGCAGCGGTCGGG

CTGAACGGGGGGTTCGTGCACACAGCCCAGCTTGGAGCGAACGACCTAC

ACCGAACTGAGATACCTACAGCGTGAGCTATGAGAAAGCGCCACGCTTC

CCGAAGGGAGAAAGGCGGACAGGTATCCGGTAAGCGGCAGGGTCGGAAC

AGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGAT

GCTCGTCAGGGGGCGGAGCCTATGGAAAAACGCCAGCAACGCGGCCTT

TTTACGGTTCCTGGGCTTTTGCTGGCCTTTTGCTCACATGTTCTT
```

Example 2

Delivery of a target molecule to the lung. A pharmaceutical composition comprising a plasmid encoding for a CFTR protein is administered to the lungs of a patient suffering from cystic fibrosis. The plasmid contains a NLS of SEQ ID NO: 19 and is linked to a constitutive promoter. The cells of the lung take up the plasmid and the CFTR protein is expressed and is found to function properly in the subject lung's cells.

Example 3

Secretion of target molecule in muscle. A pharmaceutical composition comprising a plasmid encoding for insulin protein is administered to the muscle cells of a patient suffering from Type 1 Diabetes. The plasmid contains a NLS of SEQ ID NO: 19 and is linked to a constitutive promoter. The muscle cells secrete the needed insulin, instead of the beta cells in pancreas that have been destroyed by the immune system, bringing normal functionality to the patient.

Example 4

Delivery of target molecule into bone marrow. A pharmaceutical composition comprising a plasmid encoding for glutamic acid is administered into the bone marrow, where production of red blood cells takes places. The plasmid contains a NLS of SEQ ID NO: 19 and is linked to a constitutive promoter. Sequence for glutamic acid is substituted for incorrect coding of valine at position 6 on alpha subunit in patients, bringing normal shape and functionality of red blood cells in patients.

Example 5

Delivery of target molecule into pancreas. A pharmaceutical composition comprising a plasmid encoding for growth regulating miRNA is administered into the pancreas of a patient suffering from pancreatic cancer. The plasmid contains a NLS of SEQ ID NO: 19 and is linked to a constitutive promoter. The miRNA sequence can replace lost miRNA and restore original control over cancer networks and reverse cancer aggressiveness and growth.

The examples provided for herein demonstrate the flexibility of the nucleic molecules described herein to deliver molecules and have them expressed. This can be used to simply deliver a molecule to a cell or tissue or can be used to induce an immune response against a variety of target molecules.

The examples described herein are exemplary in manner and are not intended, nor should they be used, to limit the scope of the embodiments. Each and every reference, publication, accession number, patent, document, etc., is hereby incorporated by reference in its entirety for its intended purpose.

This description is not limited to the particular processes, compositions, or methodologies described, as these may vary. The terminology used in the description is for the purpose of describing the particular versions or embodiments only, and it is not intended to limit the scope of the embodiments described herein. Unless defined otherwise, all technical and scientific terms used herein have the same meanings as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

From the foregoing, it will be appreciated that various embodiments of the present disclosure have been described herein for purposes of illustration, and that various modification can be made without departing from the scope and spirit of the present disclosure. Accordingly, the various embodiments disclosed herein are not intended to be limiting.

What is claimed is:

1. A nucleic acid molecule comprising:
   a. a polynucleotide encoding a constitutive promoter;
   b. a polynucleotide encoding a full length target protein, wherein the full-length target protein is MAGE-A2;
   c. a polynucleotide encoding a glycine-serine linker;
   d. a polynucleotide encoding a ubiquitin;
   e. a polynucleotide encoding a fragment of 7 to 25 amino acid residues of the full-length target protein; and
   f. a polynucleotide encoding a nuclear localization signal comprising the sequence of SEQ ID NO: 19,
   wherein the polynucleotides are operatively connected to one another to encode a protein comprising an amino acid sequence of the full-length target protein, an amino acid sequence of the linker, an amino acid sequence of the ubiquitin, and the fragment of 7 to 25 amino acid residues of the full-length target protein.

2. The nucleic acid molecule of claim 1, wherein the ubiquitin is a single ubiquitin protein or a chain of 2 or more ubiquitin proteins.

3. The nucleic acid molecule of claim 1, wherein the polynucleotide encoding the ubiquitin is selected from the group consisting of UBB, UBC, UBA52, and RPS27A.

4. The nucleic acid molecule of claim 1, wherein said fragment of the full-length target protein elicits an immunogenic response by MHC I or WIC II CD8+ immune cells or T-cytotoxic lymphocytes.

5. A nuclear localization signal comprising the sequence of SEQ ID NO: 19.

* * * * *

SEQUENCE LISTING

<160> NUMBER OF SEQ ID NOS: 20

<210> SEQ ID NO 1
<211> LENGTH: 720
<212> TYPE: DNA
<213> ORGANISM: Homo sapiens

<400> SEQUENCE: 1

| | | | | | |
|---|---|---|---|---|---|
| gactcttcgc | gattatcgcc | gaattcacgc | gtcgtgaggc | tcctgcaggg | ccgactagtg | 60 |
| gagccgagag | taattcatac | aaaaggaggg | atcgccttcg | caaggggaga | gcccagggac | 120 |
| cgtccctaaa | ttctcacaga | cccaaatccc | tgtagccgcc | ccacgacagc | gcgaggagca | 180 |
| tccgcccagg | gctgagcgcg | ggtagatcag | agcacacaag | ctcacagtcc | ccggcggtgg | 240 |
| ggggaggggc | gcgctgagcg | ggggccaggg | agctggcgcg | gggcaaactg | ggaaagtggt | 300 |
| gtcgtgtgct | ggctccgccc | tcttcccgag | ggtggggag | aacggtatat | aagtgcggta | 360 |
| gtcgccttgg | acgttctttt | tcgcaacggg | tttgccgtca | gaacgcagct | gaagcttcga | 420 |
| gggctcgcat | ctctccttca | cgcgcccgcc | gccctacctg | aggccgccat | ccacgccggt | 480 |
| tgagtcgcgt | tctgccgcct | cccgcctgtg | gtgcctcctg | aactgcgtcc | gccgtctagg | 540 |
| taagtttaaa | gctcaggtcg | agaccgggcc | tttgtccggc | gctcccttgg | agcctaccta | 600 |
| gactcagccg | gctctccacg | ctttgcctga | ccctgcttgc | tcaactctac | gtctttgttt | 660 |
| cgttttctgt | tctgcgccgt | tacagatcca | agccagctag | cgtttaaact | tgccgccacc | 720 |

<210> SEQ ID NO 2
<211> LENGTH: 942
<212> TYPE: DNA
<213> ORGANISM: Homo sapiens

<400> SEQUENCE: 2

| | | | | | |
|---|---|---|---|---|---|
| atgccgctcg | aacagaggag | ccagcactgt | aaaccagaag | aaggactcga | agcgaggggg | 60 |
| gaagcgttgg | ggttggtagg | tgctcaagca | ccagcaactg | aggaacagca | aactgcgagt | 120 |
| tcttcttcca | cattggtgga | agttactctt | ggggaggttc | ccgctgcgga | cagtccctcc | 180 |
| cctccacatt | cccccaggg | tgcaagttcc | tttagcacca | caatcaacta | caccctgtgg | 240 |
| cgacagtcag | atgagggaag | ttctaatcaa | gaagaagagg | ggccacgcat | gtttcccgac | 300 |
| ctcgagtctg | agttccaagc | cgctataagc | aggaagatgg | ttgagttggt | tcattttctg | 360 |
| ctcctcaagt | atcgagccag | ggagccggtc | acaaaggcag | aaatgctgga | gagtgtcctc | 420 |

| | |
|---|---:|
| agaaattgcc aggacttctt tcccgtgatc ttcagcaaag cctccgagta cttgcagctg | 480 |
| gtctttggca tcgaggtggt ggaagtggtc cccatcagcc acttatacat ccttgtcacc | 540 |
| tgcctgggcc tctcctacga tggcctgctg ggcgacaatc aggtcatgcc caagacaggc | 600 |
| ctcctgataa tcgtcctggc cataatcgca atagagggcg actgtgcccc tgaggagaaa | 660 |
| atctgggagg agctgagtat gttggaggtg tttgagggga gggaggacag tgtcttcgca | 720 |
| catcccagga agctgctcat gcaagacctg gtgcaggaaa actacctgga gtaccggcag | 780 |
| gtgcctggta gagacccagc ctgttatgaa tttctgtggg gaccaagagc acttatcgat | 840 |
| actagttatg tgaaagtcct gcaccataca ctaaagatcg gtggagaacc tcacatttcc | 900 |
| tacccacccc tgcatgaacg ggctttgaga gagggagaag ag | 942 |

<210> SEQ ID NO 3
<211> LENGTH: 314
<212> TYPE: PRT
<213> ORGANISM: Homo sapiens
<400> SEQUENCE: 3

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Gln Thr Ala Ser Ser Ser Thr Leu Val Glu Val
        35                  40                  45

Thr Leu Gly Glu Val Pro Ala Ala Asp Ser Pro Ser Pro Pro His Ser
    50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
        115                 120                 125

Pro Val Thr Lys Ala Glu Met Leu Glu Ser Val Leu Arg Asn Cys Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Glu Lys Ile Trp Glu Glu
    210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Arg Asp Pro Ala Cys Tyr Glu Phe Leu
            260                 265                 270

Trp Gly Pro Arg Ala Leu Ile Asp Thr Ser Tyr Val Lys Val Leu His
        275                 280                 285
```

His Thr Leu Lys Ile Gly Gly Glu Pro His Ile Ser Tyr Pro Pro Leu
        290                 295                 300

His Glu Arg Ala Leu Arg Glu Gly Glu Glu
305                 310

<210> SEQ ID NO 4
<211> LENGTH: 954
<212> TYPE: DNA
<213> ORGANISM: Homo sapiens

<400> SEQUENCE: 4

```
atgtcttctg agcagaagag tcagcactgc aagcctgagg aaggcgttga ggcccaagaa      60
gaggccctgg gcctggtggg tgcacaggct cctactactg aggagcagga ggctgctgtc     120
tcctcctcct ctcctctggt ccctggcacc ctggaggaag tgcctgctgc tgagtcagca     180
ggtcctcccc agagtcctca gggagcctct gccttaccca ctaccatcag cttcacttgc     240
tggaggcaac ccaatgaggg ttccagcagc aagaagagg aggggccaag cacctcgcct      300
gacgcagagt ccttgttccg agaagcactc agtaacaagg tggatgagtt ggctcatttt     360
ctgctccgca gtatcgagc caaggagctg gtcacaaagg cagaaatgct ggagagagtc      420
atcaaaaatt acaagcgctg cttcctgtg atcttcggca agcctccga gtccctgaag       480
atgatctttg gcattgacgt gaaggaagtg gaccccgcca gcaacaccta cacccttgtc     540
acctgcctgg gccttcccta tgatggcctg ctgggtaata atcagatctt tcccaagaca     600
ggccttctga taatcgtcct gggcacaatt gcaatggagg cgacagcgc tctgaggag      660
gaaatctggg aggagctggg tgtgatgggg gtgtatgatg ggagggagca cactgtctat    720
ggggagccca ggaaactgct cacccaagat tgggtgcagg aaaactacct ggagtaccgg     780
caggtacccg gcagtaatcc tgcgcgctat gagttcctgt ggggtccaag ggctctggct    840
gaaaccagct atgtgaaagt cctggagcat gtggtcaggg tcaatgcaag agttcgcatt     900
gcctacccat ccctgcgtga agcagctttg ttagaggagg aagagggagt ctga           954
```

<210> SEQ ID NO 5
<211> LENGTH: 317
<212> TYPE: PRT
<213> ORGANISM: Homo sapiens

<400> SEQUENCE: 5

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

```
Glu Leu Val Thr Lys Ala Glu Met Leu Glu Arg Val Ile Lys Asn Tyr
130                 135                 140
Lys Arg Cys Phe Pro Val Ile Phe Gly Lys Ala Ser Glu Ser Leu Lys
145                 150                 155                 160
Met Ile Phe Gly Ile Asp Val Lys Glu Val Asp Pro Ala Ser Asn Thr
                165                 170                 175
Tyr Thr Leu Val Thr Cys Leu Gly Leu Ser Tyr Asp Gly Leu Leu Gly
                180                 185                 190
Asn Asn Gln Ile Phe Pro Lys Thr Gly Leu Leu Ile Ile Val Leu Gly
            195                 200                 205
Thr Ile Ala Met Glu Gly Asp Ser Ala Ser Glu Glu Glu Ile Trp Glu
210                 215                 220
Glu Leu Gly Val Met Gly Val Tyr Asp Gly Arg Glu His Thr Val Tyr
225                 230                 235                 240
Gly Glu Pro Arg Lys Leu Leu Thr Gln Asp Trp Val Gln Glu Asn Tyr
                245                 250                 255
Leu Glu Tyr Arg Gln Val Pro Ser Asn Pro Ala Arg Tyr Glu Phe
                260                 265                 270
Leu Trp Gly Pro Arg Ala Leu Ala Glu Thr Ser Tyr Val Lys Val Leu
            275                 280                 285
Glu His Val Val Arg Val Asn Ala Arg Val Arg Ile Ala Tyr Pro Ser
290                 295                 300
Leu Arg Glu Ala Ala Leu Leu Glu Glu Glu Gly Val
305                 310                 315
```

<210> SEQ ID NO 6
<211> LENGTH: 9
<212> TYPE: PRT
<213> ORGANISM: Homo sapiens

<400> SEQUENCE: 6

```
Lys Met Val Glu Leu Val His Phe Leu
1               5
```

<210> SEQ ID NO 7
<211> LENGTH: 27
<212> TYPE: DNA
<213> ORGANISM: Homo sapiens

<400> SEQUENCE: 7
aaaatggttg aacttgttca ttttctt                                      27

<210> SEQ ID NO 8
<211> LENGTH: 9
<212> TYPE: PRT
<213> ORGANISM: Homo sapiens

<400> SEQUENCE: 8

```
Lys Val Asp Glu Leu Ala His Phe Leu
1               5
```

<210> SEQ ID NO 9
<211> LENGTH: 27
<212> TYPE: DNA
<213> ORGANISM: Homo sapiens

<400> SEQUENCE: 9
aaggtggatg agttggctca ttttctg                                      27

<210> SEQ ID NO 10
<211> LENGTH: 5
<212> TYPE: PRT
<213> ORGANISM: Artificial Sequence
<220> FEATURE:
<223> OTHER INFORMATION: synthetic sequence

<400> SEQUENCE: 10

Gly Gly Gly Gly Ala
1               5

<210> SEQ ID NO 11
<211> LENGTH: 15
<212> TYPE: PRT
<213> ORGANISM: Artificial Sequence
<220> FEATURE:
<223> OTHER INFORMATION: synthetic seqeunce

<400> SEQUENCE: 11

Gly Gly Gly Gly Ser Gly Gly Gly Ala Gly Gly Gly Ser
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: synthetic sequence

<400> SEQUENCE: 12

Gly Gly Ser Gly Ser
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic sequence

<400> SEQUENCE: 13

Gly Gly Gly Gly Ser
1               5

<210> SEQ ID NO 14
<211> LENGTH: 76
<212> TYPE: PRT
<213> ORGANISM: Homo sapiens

<400> SEQUENCE: 14

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 15
<211> LENGTH: 228
<212> TYPE: DNA
<213> ORGANISM: Homo sapiens

<400> SEQUENCE: 15

```
atgcagatct tcgtgaagac gttaaccggt aaaaccataa ctctcgaagt tgaaccatcc      60
gataccatcg aaaacgttaa ggctaaaatt caagacaagg aaggcattcc acctgatcaa     120
caaagattga tctttgccgg taagcagctg gaggacggta gaacgctgtc tgattacaac     180
attcagaagg agtcgacctt acatcttgtc ttaagactaa gaggtggt                  228
```

<210> SEQ ID NO 16
<211> LENGTH: 685
<212> TYPE: PRT
<213> ORGANISM: Homo sapiens

<400> SEQUENCE: 16

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320
```

```
Val Glu Pro Ser Asp Thr Ile Glu Asn Val Lys Ala Lys Ile Gln Asp
            325                 330                 335

Lys Glu Gly Ile Pro Pro Asp Gln Gln Arg Leu Ile Phe Ala Gly Lys
        340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
        420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
        500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
    530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
            565                 570                 575

Phe Ala Gly Lys Gln Leu Glu Asp Gly Arg Thr Leu Ser Asp Tyr Asn
        580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
    610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
            645                 650                 655

Gln Leu Glu Asp Gly Arg Thr Leu Ser Asp Tyr Asn Ile Gln Lys Glu
        660                 665                 670

Ser Thr Leu His Leu Val Leu Arg Leu Arg Gly Gly Val
        675                 680                 685

<210> SEQ ID NO 17
<211> LENGTH: 128
<212> TYPE: PRT
<213> ORGANISM: Homo sapiens

<400> SEQUENCE: 17

Met Gln Ile Phe Val Lys Thr Leu Thr Gly Lys Thr Ile Thr Leu Glu
1               5                   10                  15
```

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ile Ile Glu Pro
65                  70                  75                  80

Ser Leu Arg Gln Leu Ala Gln Lys Tyr Asn Cys Asp Lys Met Ile Cys
                85                  90                  95

Arg Lys Cys Tyr Ala Arg Leu His Pro Arg Ala Val Asn Cys Arg Lys
            100                 105                 110

Lys Lys Cys Gly His Thr Asn Asn Leu Arg Pro Lys Lys Lys Val Lys
        115                 120                 125

<210> SEQ ID NO 18
<211> LENGTH: 156
<212> TYPE: PRT
<213> ORGANISM: Homo sapiens

<400> SEQUENCE: 18

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
        115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155

<210> SEQ ID NO 19
<211> LENGTH: 105
<212> TYPE: DNA
<213> ORGANISM: Homo sapiens

<400> SEQUENCE: 19
cacaattcca cacatgtgtg aaattgttat ccgctcacaa ttccacacat gtgtgaaatt    60
gttatccgct cacaattcca cacacgtg ctaaaacttc atttt                     105

<210> SEQ ID NO 20
<211> LENGTH: 4259
<212> TYPE: DNA
<213> ORGANISM: Artificial Sequence
<220> FEATURE:
<223> OTHER INFORMATION: synthetic sequence

<400> SEQUENCE: 20

```
gactcttcgc gattatcgcc gaattcacgc gtcgtgaggc tcctgcaggg ccgactagtg      60
gagccgagag taattcatac aaaaggaggg atcgccttcg caaggggaga gcccagggac     120
cgtccctaaa ttctcacaga cccaaatccc tgtagccgcc ccacgacagc gcgaggagca     180
tccgcccagg gctgagcgcg ggtagatcag agcacacaag ctcacagtcc ccggcggtgg     240
ggggaggggc gcgctgagcg ggggccaggg agctggcgcg gggcaaactg gaaagtggt      300
gtcgtgtgct ggctccgccc tcttcccgag ggtgggggag aacggtatat aagtgcggta     360
gtcgccttgg acgttctttt tcgcaacggg tttgccgtca gaacgcagct gaagcttcga     420
gggctcgcat ctctccttca cgcgcccgcc gccctacctg aggccgccat ccacgccggt     480
tgagtcgcgt tctgccgcct cccgcctgtg gtgcctcctg aactgcgtcc gccgtctagg     540
taagtttaaa gctcaggtcg agaccgggcc tttgtccggc gctcccttgg agcctaccta     600
gactcagccg gctctccacg ctttgcctga ccctgcttgc tcaactctac gtctttgttt     660
cgttttctgt tctgcgccgt tacagatcca agccagctag cgtttaaact tgccgccacc     720
atgccgctcg aacagaggag ccagcactgt aaaccagaag aaggactcga agcgagggg      780
gaagcgttgg ggttggtagg tgctcaagca ccagcaactg aggaacagca aactgcgagt     840
tcttcttcca cattggtgga agttactctt ggggaggttc ccgctgcgga cagtccctcc     900
cctccacatt ccccccaggg tgcaagttcc tttagcacca caatcaacta caccctgtgg     960
cgacagtcag atgagggaag ttctaatcaa gaagaagagg ggccacgcat gtttcccgac    1020
ctcgagtctg agttccaagc cgctataagc aggaagatgg ttgagttggt tcatttctg     1080
ctcctcaagt atcgagccag ggagccggtc acaaaggcag aaatgctgga gagtgtcctc    1140
agaaattgcc aggacttctt tcccgtgatc ttcagcaaag cctccgagta cttgcagctg    1200
gtctttggca tcgaggtggt ggaagtggtc cccatcagcc acttatacat ccttgtcacc    1260
tgcctgggcc tctcctacga tggcctgctg ggcgacaatc aggtcatgcc caagacaggc    1320
ctcctgataa tcgtcctggc cataatcgca atagagggcg actgtgcccc tgaggagaaa    1380
atctgggagg agctgagtat gttggaggtg tttgagggga gggaggacag tgtcttcgca    1440
catcccagga agctgctcat gcaagacctg gtgcaggaaa actacctgga gtaccggcag    1500
gtgcctggta gagacccagc ctgttatgaa tttctgtggg gaccaagagc acttatcgat    1560
actagttatg tgaaagtcct gcaccataca ctaaagatcg gtggagaacc tcacatttcc    1620
tacccacccc tgcatgaacg ggcttttgaga gaggagaag agggtggttc tggtagcatg    1680
cagatcttcg tgaagacgtt aaccggtaaa accataactc tcgaagttga accatccgat    1740
accatcgaaa acgttaaggc taaaattcaa gacaaggaag cattccaccc tgatcaacaa    1800
agattgatct tgccggtaa gcagctggag gacggtagaa cgctgtctga ttacaacatt    1860
cagaaggagt cgaccttaca tcttgtctta agactaagag gtggtaaaat ggttgaactt    1920
gttcattttc tttgactcga gcgcgctggg cccttttaaac ccgctgatca gcctcgaccg    1980
tgccttctag ttgccagcca tctgttgttt gcccctcccc cgtgccttcc ttgaccctgg    2040
aaggtgccac tcccactgtc ctttcctaat aaaatgagga aattgcatcg cattgtctga    2100
gtaggtgtca ttctattctg gggggtgggg tggggcagga cagcaagggg aggattggg     2160
aagacaatag caggcatgct ggggatgcgg tgggctctat ggcttctact gggcggtttt    2220
atggacagca agcgaaccgg aattgccagc tggggcgccc tctggtaagg ttgggaagcc    2280
```

```
ctgcaaagta aactggatgg ctttctcgcc gccaaggatc tgatggcgca ggggatcaag    2340
ctctgatcaa gagacaggat gaggatcgtt tcgcatgatt gaacaagatg gattgcacgc    2400
aggttctccg gccgcttggg tggagaggct attcggctat gactgggcac aacagacaat    2460
cggctgctct gatgccgccg tgttccggct gtcagcgcag gggcgcccgg ttcttttttgt   2520 caagaccgac ctgtccggtg ccctgaatga actgcaagac gaggcagcgc ggctatcgtg    2580
gctggccacg acgggcgttc cttgcgcagc tgtgctcgac gttgtcactg aagcgggaag    2640
ggactggctg ctattgggcg aagtgccggg gcaggatctc ctgtcatctc accttgctcc    2700
tgccgagaaa gtatccatca tggctgatgc aatgcggcgg ctgcatacgc ttgatccggc    2760
tacctgccca ttcgaccacc aagcgaaaca tcgcatcgag cgagcacgta ctcggatgga    2820
agccggtctt gtcgatcagg atgatctgga cgaagagcat caggggctcg cgccagccga    2880
actgttcgcc aggctcaagg cgagcatgcc cgacggcgag gatctcgtcg tgacccatgg    2940
cgatgcctgc ttgccgaata tcatggtgga aaatggccgc ttttctggat tcatcgactg    3000
tggccggctg ggtgtggcgg accgctatca ggacatagcg ttggctaccc gtgatattgc    3060
tgaagagctt ggcggcgaat gggctgaccg cttcctcgtg ctttacggta tcgccgctcc    3120
cgattcgcag cgcatcgcct tctatcgcct tcttgacgag ttcttctgaa ttattaacgc    3180
ttacaatttc ctgatgcggt attttctcct tacgcatctg tgcggtattt cacaccgcat    3240
acaggtggca cttttcgggg aaatgtgcgc ggaaccccta tttgtttatt tttctaaata    3300
cattcaaata tgtatccgct catgagacaa taaccctgat aaatgcttca ataatagcac    3360
gtgtgtgtga aattgttatc cgctcacaat tccacacatg tgtgaaattg ttatccgctc    3420
acaattccac acatgtgtga attgttatc cgctcacaat tccacacaca cgtgctaaaa    3480
cttcattttt aatttaaaag gatctaggtg aagatccttt ttgataatct catgaccaaa    3540
atcccttaac gtgagttttc gttccactga gcgtcagacc ccgtagaaaa gatcaaagga    3600
tcttcttgag atcctttttt tctgcgcgta atctgctgct tgcaaacaaa aaaaccaccg    3660
ctaccagcgg tggtttgttt gccggatcaa gagctaccaa ctcttttttcc gaaggtaact    3720 ggcttcagca gagcgcagat accaaatact gtccttctag tgtagccgta gttaggccac    3780
cacttcaaga actctgtagc accgcctaca tacctcgctc tgctaatcct gttaccagtg    3840
gctgctgcca gtggcgataa gtcgtgtctt accgggttgg actcaagacg atagttaccg    3900
gataaggcgc agcggtcggg ctgaacgggg ggttcgtgca cacagcccag cttggagcga    3960
acgacctaca ccgaactgag atacctacag cgtgagctat gagaaagcgc cacgcttccc    4020
gaagggagaa aggcggacag gtatccggta agcggcaggg tcggaacagg agagcgcacg    4080
agggagcttc caggggggaaa cgcctggtat ctttatagtc ctgtcgggtt tcgccacctc    4140
tgacttgagc gtcgattttt gtgatgctcg tcaggggggc ggagcctatg gaaaaacgcc    4200
agcaacgcgg cctttttacg gttcctgggc ttttgctggc cttttgctca catgttcttc    4259
```